United States Patent
Yamaguchi et al.

(10) Patent No.: US 7,744,918 B2
(45) Date of Patent: Jun. 29, 2010

(54) DRUG-CONTAINING PATCH

(75) Inventors: Toshiro Yamaguchi, Tsukuba (JP);
Mitsuru Kuribayashi, Tsukuba (JP)

(73) Assignee: Hisamitsu Pharmaceutical Co., Inc., Tosu-Shi, Saga (JP)

( * ) Notice: Subject to any disclaimer, the term of this patent is extended or adjusted under 35 U.S.C. 154(b) by 1224 days.

(21) Appl. No.: 11/284,357

(22) Filed: Nov. 21, 2005

(65) Prior Publication Data

US 2006/0110434 A1 May 25, 2006

(30) Foreign Application Priority Data

Nov. 22, 2004 (JP) .............................. 2004/336871

(51) Int. Cl.
*A61F 13/00* (2006.01)
*A61K 9/70* (2006.01)

(52) U.S. Cl. ....................... 424/443; 424/400; 424/445; 424/447

(58) Field of Classification Search ........................ None
See application file for complete search history.

(56) References Cited

U.S. PATENT DOCUMENTS

| 4,804,663 | A | | 2/1989 | Kennis et al. ................ 514/258 |
| 5,830,497 | A | * | 11/1998 | Yamanaka et al. ........... 424/448 |
| 5,866,157 | A | * | 2/1999 | Higo et al. ................... 424/448 |
| 2003/0124176 | A1 | | 7/2003 | Hsu et al. .................... 424/449 |
| 2004/0220262 | A1 | | 11/2004 | Hsu et al. .................... 514/536 |
| 2007/0134310 | A1 | * | 6/2007 | Nedberge et al. ............ 424/449 |

FOREIGN PATENT DOCUMENTS

| EP | 0 788 792 A1 | 8/1997 |
| EP | 0 842 662 A1 | 5/1998 |
| EP | 1 074 251 A1 | 2/2001 |
| EP | 1 170 004 A1 | 1/2002 |
| EP | 1 201 232 A1 | 5/2002 |
| JP | 6-13511 | 2/1994 |
| JP | 11-302161 | 2/1999 |
| JP | 11-503138 | 3/1999 |
| JP | 2001-511782 | 8/2001 |
| JP | 2003-525865 | 9/2003 |
| JP | 2005-082512 | 3/2005 |
| WO | WO 96/31201 | 10/1996 |
| WO | WO96/31201 | 10/1996 |
| WO | WO98/31335 | 7/1998 |
| WO | WO00/54764 | 9/2000 |
| WO | WO00/61120 | 10/2000 |
| WO | WO01/07018 A1 | 1/2001 |

* cited by examiner

*Primary Examiner*—Robert A Wax
*Assistant Examiner*—Melissa S Mercier
(74) *Attorney, Agent, or Firm*—Licata & Tyrell P.C.

(57) ABSTRACT

The problem of the invention is to provide a drug-containing patch which is very favorable in percutaneous absorbability and is excellent in sustainability of the drug efficacy, that is, the drug-containing patch having a sufficient percutaneous absorbability and effect sustainability in a degree to be actually used for therapy of patients. The problem is solved by a patch comprising a drug, a melting point lowering agent and an adhesive base.

9 Claims, No Drawings

DRUG-CONTAINING PATCH

This patent application is a continuation of Japanese Patent Application No. 2004-336871, filed Nov. 22, 2004, teachings of which are herein incorporated by reference in their entirety.

TECHNICAL FIELD

The invention relates to a patch for an external use containing a drug.

BACKGROUND ART

Risperidone is a benzoisoxazole derivative developed by Janssen Pharmaceutical (Belgium) (see patent document 1). As pharmacological actions of risperidone, the anti-dopaminergic action, the anti-serotonergic action and the catalepsy inducing action have been confirmed. At present besides being widely used in clinical practice as an antischizophrenia drug, use in treatment for hyperphagia, a cosmetic composition for treatment of a sensitive skin and the like have been proposed (see Patent Documents 2 and 3).

It is considered that the effect of risperidone against schizophrenia is due to adjustment of the central nervous system mainly based on dopamine $D_2$ receptor antagonistic action and serotonin 5-$HT_2$ receptor antagonistic action. In addition, risperidone shows an excellent effect against positive symptoms such as hallucination and delusion as well as a strong effect against negative symptoms such as an emotional social withdrawal and a blunted affect, while it has characteristics that it shows relatively few side effects of the pyramidal tract (chill, stiffness, etc.) compared with a conventional typical antipsychotic agent, and therefore, it is considered to be an extremely useful antischizophrenia drug which can tremendously improve the QOL (quality of life) of patients.

As an administration method for risperidone, an oral administration method using tablets, fine granules, a liquid preparation for internal use has been used. However, the oral administration has some drawbacks such as susceptibility to a first-pass effect in the liver after absorption of the drug and an observation of a temporary and unnecessary high blood concentration after the administration. In addition, in the oral administration many side effects such as a gastrointestinal tract disorder, a vomiting feeling and a loss of appetite have been reported. Further, in schizophrenia patients, it is said that actually about 75% of them have difficulties to take an oral preparation regularly. Therefore, with the aim of solving such problems in the oral administration and making a preparation which patients can easily take with safety and persistence, administration methods using patches have been examined in recent years. An administration method using a patch can dissolve the above various problems in oral administration methods and has advantages such as reduction of administration frequency, improvement in compliance, and easiness of administration and discontinuation, therefore, it has been expected as an useful administration method.

However, because, in the horny layer, keratin-containing cells and an intercellular lipid are laminated in layers, permeability of a drug is generally extremely low, and in addition to this, because the horny layer of a normal skin has a barrier function to prevent invasion of foreign substances into the body, only blending risperidone in an adhesive layer composition of the conventional patch could not give a risperidone-containing patch having a sufficient skin absorbability.

Therefore, to increase the skin absorbability of risperidone in a percutaneous administration method using a patch, a patch containing a skin permeation enhancer such as fatty acids or solvent such as propylene glycol together with risperidone has been proposed (see patent document 4). However, even with these attempts, the skin absorbability of risperidone blended in a patch is not sufficient, and actually, a patch containing risperidone has not yet been on the market. Therefore, development of a preparation, which has an excellent percutaneous absorbability and sustainability to the possible extent for therapeutic use, has been desired.

On the other hand, in a percutaneous absorption preparation containing a basic drug, it was already proposed that a skin permeability of the basic drug was improved by blending an organic acid salt or an organic acid with the basic drug (see patent documents 5-7). However, in these documents, although hypnotic-sedative agents, psychotropic agents and the like are exemplified as the basic drugs, there was no suggestion whether a drug-containing patch could actually be prepared as an effective preparation having a sufficient skin absorbability to the possible extent for therapeutic use for patients. In addition, an external preparation whose skin absorbability was enhanced by formation of an ionic liquid between an ionic drug and a substance to be an counter ion was already proposed (see patent document 8); as ionic drugs, only indomethacin, diclofenac sodium, sodium cromoglycate, tramadol hydrochloride and piroxicam were exemplified. Further, the literature described that the melting point of the ionic liquid, which was prepared with indomethacin or diclofenac sodium as the ionic drug and lidocaine or lidocaine hydrochloride as a substance to be the counter ion, lowered. However, the lowering of basic drugs is not specifically disclosed since both indomethacin and diclofenac are acid drugs. Additionaly, although an ointment containing indomethacin or diclofenac sodium as the ionic drug and being blended with lidocaine or lidocaine hydrochloride as a substance to be the counter ion is disclosed, there is no suggestion in any way whether a patch containing such ionic liquid of the drug can achieve a sufficient skin absorbability and sustainability.

Patent document 1: JP, B, 6-13511
Patent document 2: JP, A, 2003-525865
Patent document 3: JP, A, 2001-511782
Patent document 4: JP, A, 11-503138
Patent document 5: JP, A, 11-302161
Patent document 6: WO00/61120
Patent document 7: WO01/007018
Patent document 8: JP, A, 2005-82512

DISCLOSURE OF THE INVENTION

Problem to be Solved by the Invention

Consequently, the problem of the invention is to provide a drug-containing patch which is very favorable in percutaneous absorbability and is excellent in sustainability of the drug efficacy, that is, the drug-containing patch having a sufficient percutaneous absorbability and effect sustainability to the possible extent for an actual therapeutic use for patients.

Means for Solving Problem

During extensive research to solve the above problems with the aim of improving percutaneous absorbability of drugs, especially focusing on risperidone, the inventors found that, by blending a specific drug with a melting point lowering agent to lower the melting point of said drug in an adhesive base, the percutaneous absorbability of the drug and sustainability of the drug efficacy is significantly improved, and as a result of further investigation, the inventors completed the invention.

Namely, the invention relates to a patch comprising a drug, a melting point lowering agent and an adhesive base.

In addition, the invention relates to the above patch, wherein the melting point lowering agent lowers the melting point of the drug by 60° C. or more.

Further, the invention relates to the above patch, wherein the melting point lowering agent is one or more kinds selected from a group consisting of acetic acid, propionic acid, butyric acid, lactic acid, benzoic acid, salicylic acid, and salts thereof.

Furthermore, the invention relates to the above patch, wherein the melting point lowering agent is acetic acid and/or sodium acetate.

Additionally, the invention relates to the above patch, wherein the drug is a basic drug.

Further, the invention relates to the above patch, wherein the basic drug is selected from a group consisting of oxybutynin, fentanyl, pergolide, tandospirone, donepezil, tamsulosin, risperidone, flurazepam, butorphanol, perisoxal, pridinol, trihexyphenidyl, amantadine, tulobuterol, isoprenaline, propranolol, ketotifen, difenidol, morphine, meloxicam, valdecoxib and celecoxib.

The invention also relates to the above patch, wherein the basic drug is risperidone.

Furthermore, the invention relates to the above patch, wherein the adhesive base contains a styrene-isoprene-styrene block copolymer and/or an acrylate copolymer.

In addition, the invention relates to the above patch, wherein it further contains one or more kinds selected from a group consisting of lauric acid diethanolamide, capric acid, isopropyl myristate and propylene glycol monolaurate as an absorption enhancer.

Namely, a patch of the above constitution containing a drug and a melting point lowering agent makes a drug come to the form of an addition salt of the melting point lowering agent via an ion-pair formation in an adhesive layer, whereby the patch of the invention, which was very excellent in percutaneous absorbability and sustainability of the drug efficacy, was achieved by realizing the improvement of the drug stability of and the tremendous lowering of the melting point; and the problem of the invention was solved.

Effect of the Invention

In a patch of the invention, by blending a specific drug and a melting point lowering agent to lower the melting point of the drug in an adhesive layer, the skin absorbability of the drug blended in the patch is significantly improved compared with a conventional patch in which a sufficient percutaneous absorbability could not be achieved, attaining a preparation with extremely excellent skin absorbability. In addition, it is possible to make the percutaneous absorbability of the drug more excellent by blending further a specific absorption enhancer into a patch of the invention.

In addition, by administration of a drug such as risperidone, which has been administered as a conventional oral preparation, using an external patch of the invention, such a drug can be administered as a preparation excellent in sustainability of the drug efficacy, without being subjected to decomposition in the digestive organs and metabolism in the liver. Therefore, the patch of the invention can simplify a conventional administration method and improve compliance, whereby a very low compliance with treatment in schizophrenia patients and the like can also be improved greatly.

Namely, in a patch of the invention, a drug blended in the patch is percutaneously absorbed sufficiently and the sustainability of the effect is also excellent, and consequently, the drug effect can sufficiently be exhibited. Further, a drug-containing patch having the constitution that a drug and a melting point lowering agent to lower the melting point of the drug were contained in an adhesive layer, was achieved for the first time in the invention, and therefore, a drug-containing patch showing the above effects was also realized for the first time in the invention.

BEST EMBODIMENT FOR CARRYING OUT THE INVENTION

In the following, the embodiment of the invention is illustrated in detail.

A drug used in the invention is not limited, as long as it is solid at room temperature, but it may include antiinflammatory drugs, analgesic drugs, antiallergy drugs, cardiotonic drugs, bronchodilators, muscle relaxants, antidizziness drugs, antiarrhythmic drugs, antiparkinson drugs, antipsychotic drugs, antidepressant drugs, antianxiety drugs, antiemetic drugs, expectorants, antipollakiuria drugs, anesthetics, antidementia drugs, antihypertensive drugs, hypnotic-sedative drugs, antimigraine drugs, exitation-analeptic drugs, autonomic drugs and the like. Those can be used in the form of a free acid, free base and/or pharmaceutically acceptable salts thereof. A basic drug is preferable as the drug used in the invention. Additionaly, as the basic drug, oxybutynin, fentanyl, pergolide, tandospirone, donepezil, tamsulosin, risperidone, flurazepam, butorphanol, perisoxal, pridinol, trihexyphenidyl, amantadine, tulobuterol, isoprenaline, propranolol, ketotifen, difenidol, morphine, meloxicam, or valdecoxib, celecoxib is more preferable and among these, risperidone is particularly preferable. Risperidone can be used in a free base and/or its pharmaceutically acceptable salts. Further, the pharmaceutically acceptable salts are not particularly limited and may be an inorganic salt or an organic salt. In addition, risperidone in the form of free base is blended with a melting point lowering agent together with an adhesive base and the like and produced as a patch in which risperidone is preferably present in the form of an acid addition salt of the melting point lowering agent.

From the viewpoint of physical properties of a pharmaceutical preparation and percutaneous absorbability, the drug and/or its pharmaceutically acceptable salts are preferably blended with 3-30 wt. % based on the weight of the total composition of the adhesive layer, more preferably 5-20 wt. %, in particular preferably 10-20 wt. %.

In addition, other pharmaceutically effective ingredients may be contained, if necessary. Such pharmaceutically efficacious ingredients are not particularly limited, though those may include, for example, antiinflammatory drugs, analgesic drugs, antiallergy drugs, cardiotonic drugs, bronchodilators, muscle relaxants, antidizziness drugs, antiarrhythmic drugs, antiparkinson drugs, antipsychotic drugs, antidepressant drugs, antianxiety drugs, antiemetic drugs, expectorants, antipollakiuria drugs, anesthetics, antidementia drugs, antihypertensive drugs, hypnotic-sedative drugs, antimigraine drugs, exitation-analeptic drugs, autonomic drugs, etc.

A melting point lowering agent used in the patch of the invention is not limited in particular, as long as the melting point of the drug can be lowered by blending it with the drug in the composition of the adhesive layer. Lowering the melting point of the drug substantially makes the motion of the drug molecule freer, and thereby the absorbability of the drug can increase. Particularly, the melting point lowering agent lowers the melting point of the drug preferably by 60° C. or more, more preferably by 90° C. or more, in particular preferably by 120° C. or more.

For example, in case of a basic drug, an organic acid and/or its salts are preferably used, and in particular, $C_2$-$C_7$ carboxylic acids and/or salts thereof are preferable. Such $C_2$-$C_7$ carboxylic acids may include aliphatic (mono-, di- or tri-) carboxylic acids (e.g., acetic acid, propionic acid, butyric acid, lactic acid, maleic acid, fumaric acid, pyruvic acid, oxalic acid, succinic acid, tartaric acid, etc.), aromatic carboxylic acids (e.g., salicylic acid, benzoic acid, etc.) and the like. Further, among these, acetic acid, propionic acid, butyric acid, lactic acid, benzoic acid and salicylic acid are preferable, and acetic acid is particularly preferable. As the organic acid salts, they may be inorganic salts or organic salts of such acids, though salts of acetic acid, salts of propionic acids, salts of butyric acid, salts of lactic acids, salts of benzoic acid or salts of salicylic acid are preferable, and sodium acetate is particularly preferable.

Among these, a preferable melting point lowering agent which is an acid has action to dissolve free base of the drug and tremendously lowers the melting point of the basic drug. Lowering of the melting point means that the intermolecular interaction energy of the basic drug in a crystalline state decreases. Since crystallization and dissolution of molecules are phenomenon occurring in equilibrium, lowering of melting point is believed to act to relieve the restriction of molecular motion. Therefore, in the case that the drug is present as a form of acid addition salt of a melting point lowering agent in the adhesive layer, it is believed that a high percutaneous absorbability can be realized, because the restriction of molecular motion in the adhesive layer is relieved compared with the case that it exists as the free base form.

In addition, the above-mentioned preferable melting point lowering agents which are acids increase the solubility of free base of the basic drug into the adhesive layer. This is because by adding the melting point lowering agent with the basic drug, the melting point lowering agent of acid releases $H^+$ to become the minus ion, and subsequently the released $H^+$ forms (drug-$H^+$) with the basic drug and stably produces an ion-pair with the minus ion of the melting point lowering agent, and thereby it becomes seemingly low in polarity compared with the free base drug, although the free base drug has low solubility in a non-polar adhesive base and the like as it has polarity. Further, these preferable melting point lowering agents which are acids have action to plasticize the adhesive layer. Therefore, using these preferable melting point lowering agents can make the diffusion rate to the skin side increase as well as can make the solubility of free base drug into the adhesive base enhance.

Meanwhile, in case that the basic drug is not free base but an addition salt of a certain acid, a salt of an organic acid which is the above preferable melting point lowering agent can be blended with an adhesive base as the melting point lowering agent. This makes the basic drug come to an addition salt of an acid in the adhesive layer, which is the melting point lowering agent, whereby the melting point of the drug lowers in the same way as the above case and the permeability of the drug into the skin increases greatly. For example, when an acid (acid which is not a melting point lowering agent) addition salt of risperidone and sodium acetate are blended with an adhesive base, risperidone exists as risperidone acetate in an adhesive layer, and its melting point lowering results in production of a patch having an excellent skin permeability.

These melting point lowering agents may be used in one kind alone or in two or more kinds in combination. In addition, the blend amount of these melting point lowering agents is preferably 0.5-5 mole, more preferably 1-4 mole, in particular preferably 1-3 mole against 1 mole of the drug, considering the stability and skin permeability as an external patch and the adhesive properties of the preparation. This is due to the fact that there is a tendency of reduction of the percutaneous absorbability when the mole ratio of the melting point lowering agent against the drug is less than 0.5 and there is a tendency of reduction of cohesive and adhesive properties of an adhesive layer when the mole ratio exceeds 5.

In addition, in case that a melting point lowering agent used in the patch of the invention is an acid (that is, in case that the form of free base as the basic drug is used), it is preferable to further contain a melting point lowering agent, which is a corresponding salt of the acid. In the patch of the invention, such a salt may be an inorganic salt or an organic salt of the corresponding acid. Therefore, for example, when acetic acid is used as the melting point lowering agent, it is preferable to further contain salt of acetic acid (e.g., sodium acetate). During preparation or storage of a patch or during an application period, a melting point lowering agent which is one of the above acids may volatilize and this is a very big problem, considering that the melting point lowering agent plays an important role in the absorbability to the skin as described above. However, further containing a salt of the acid melting point lowering agent makes it possible to suppress effectively reduction of the content of the melting point lowering agent in an adhesive layer composition or an adhesive layer, and a patch which can stably exhibit an excellent percutaneous absorbability and sustainability of the drug efficacy can be provided.

In such a case, the blend amount of a salt of the melting point lowering agent which is a salt is preferably 0.5-5 as the mole ratio against the basic drug, more preferably 1-4, in particular preferably 2-3.

An adhesive base used in the invention is not limited in particular as long as it can be a base of the adhesive layer, but it may include, for example, hydrophobic polymers, such as styrene-isoprene-styrene block copolymer (hereinafter abbreviated as SIS), isoprene rubber, polyisobutylene (hereinafter abbreviated as PIB), styrene-butadiene-styrene block copolymer (hereinafter abbreviated as SBS), styrene-butadiene rubber (hereinafter abbreviated as SBR), acrylate copolymer (copolymer of at least two selected from a group consisting of 2-ethylhexyl acrylate, vinyl acetate, methacrylate, methoxyethyl acrylate, hydroxyethyl acrylate and acrylic acid) or polydimethylsiloxane. Among these, SIS and acrylate copolymer are particularly preferable.

These adhesive bases may be used in one kind alone or in two or more kinds in combination. In addition, the blend amount of the adhesive bases is preferably 5-50 wt. % based on the weight of the total composition of the adhesive layer, more preferably 10-40 wt. %, in particular preferably 10-30 wt. %, considering formation of the adhesive layer and permeability of an effective ingredient into the skin.

As for the patch of the invention, an absorption enhancer to further enhance the percutaneous absorbability of a pharmaceutically effective ingredient may be contained besides the above essential ingredients (a drug, a melting point lowering agent and an adhesive base). As the absorption enhancer used in the invention, for example, it may include $C_6$-$C_{20}$ fatty acids, fatty alcohols, fatty acid esters, ethers, or amides, aromatic organic acids, aromatic alcohols, aromatic organic acid esters or ethers (those heretofore described may be either saturated or unsaturated, and either cyclic, linear or branched), furthermore, lactic acid esters, acetic acid esters, monoterpene compounds, sesquiterpene compounds, Azone, Azone derivatives, glycerin fatty acid esters, sorbitan fatty acid esters (Span), polysorbates (Tween), polyethylene glycol fatty acid esters, polyoxyethylene hardened caster oils (HCO), sucrose fatty acid esters and the like. Among these, lauric diethanolamide, capric acid, isopropyl myristate and propylene glycol monolaurate are particularly preferable because they greatly improve the percutaneous absorbability of the patch of the invention by blend with the adhesive layer composition of the invention.

These absorption enhancers may be used in one kind alone or in two or more kinds in combination. In addition, the blend amount of the absorption enhancers is preferably 1-10 wt. % based on the weight of the total composition of the adhesive layer, more preferably 2-8 wt. %, in particular preferably 3-6 wt. %, considering a sufficient permeability of an effective ingredient to the skin, irritation to the skin and the like as the patch.

In addition, in the adhesive layer of the patch of the invention, it is desirable that a tackifying resin is further blended in case of insufficient adhesive force. Usable tackifying resins may include rosin derivatives (e.g., rosin, glycerol esters of rosin, hydrogenated rosin, glycerol esters of hydrogenated rosin, pentaerythritol esters of rosin and the like), alicyclic saturated hydrocarbon resins (e.g., ARKON P-100, manufactured by Arakawa Chemical Industries), aliphatic hydrocarbon resins (e.g., Quintone B 170, manufactured by Zeon Corporation), terpene resins (e.g., Clearon P-125, manufactured by Yasuhara Chemical), maleic acid resins and the like. Among these, particularly preferable tackifying resins are glycerol esters of hydrogenated rosin, alicyclic saturated hydrocarbon resins, aliphatic hydrocarbon resins and terpene resins.

These tackifying resins may be used in one kind alone or in two or more kinds in combination. In addition, the blend amount of the tackifying resins is preferably 20-60 wt. % based on the weight of the total composition of the adhesive layer, more preferably 30-60 wt. %, in particular preferably 40-60 wt. %, considering a sufficient adhesive force as a patch and physical irritation to the skin when peeling off the patch.

Further, a plasticizer may be blended in the patch of the invention. Plasticizers used in the invention may include petroleum oil (e.g., paraffinic processed oil, naphthenic processed oil, aromatic processed oil, etc.), squalane, squalene, vegetable oil (e.g., olive oil, camellia oil, caster oil, tall oil, arachis oil), dibasic acid ester (e.g., dibutyl phthalate, dioctylphthalate, etc.), liquid rubber (e.g., polybutene, liquid isoprene rubber), diethylene glycol, polyethylene glycol, glycol salicylate, propylene glycol, dipropylene glycol, crotamiton, etc. Among these, liquid paraffin, liquid polybutene, glycol salicylate and crotamiton are particularly preferable.

These plasticizers may be used in one kind alone or in two or more kinds in combination. The blend amount of the plasticizers is preferably 5-30 wt. % based on the weight of the total composition of the adhesive layer, more preferably 10-30 wt. %, in particular preferably 10-20 wt. %, considering a sufficient skin permeability of an effective ingredient and maintenance of sufficient cohesive force as a patch.

In addition, if necessary, an antioxidant, filler, cross-linking agent, preservative or UV absorber can be blended in the patch of the invention. As antioxidants, tocopherol and its ester derivatives, ascorbic acid, ascorbic acid-stearic acid ester, nordihydroguaretic acid, dibutyl hydroxy toluene (BHT), butyl hydroxy anisole and the like are preferable. As fillers, calciumcarbonate, magnesiumcarbonate, silicates (e.g., aluminum silicate, magnesiumsilicate, etc.), silicic acid, bariumsulfate, calcium sulfate, calcium zincate, zinc oxide, titanium oxide and the like are preferable. As cross-linking agents, amino compounds, phenol compounds, epoxy compounds, isocyanate compounds, organic peroxides, metal alcoholate, metal chelate and the like are preferable. As preservatives, ethyl p-hydroxybenzoate, propyl p-hydroxybenzoate, butyl p-hydroxybenzoate and the like are preferable. As ultraviolet absorbers, p-aminobenzoic acid derivatives, anthranilic acid derivatives, salicylic acid derivatives, coumarin derivatives, amino acid compounds, imidazoline derivatives, pyrimidine derivatives, dioxane derivatives and the like are preferable.

Such an antioxidant, filler, cross-linking agent, preservative and ultraviolet absorber in total may be blended preferably in 10 wt. % or less, more preferably in 5 wt. % or less, in particular preferably in 2 wt. % or less, based on the total composition of the adhesive layer.

A patch of the invention that contains an adhesive layer with the above composition containing a drug may be prepared by any known method; for example, a drug and a melting point lowering agent together with an adhesive base are dissolved in solvent such as dichloromethane, toluene, hexane or ethyl acetate, and the mixture is spread on a release liner or a backing and the solvent is removed by drying, then the resultant is attached to the backing or the release liner.

The backing of the patch of the invention is not particularly limited as long as it is appropriate for supporting the adhesive layer; a stretch or nonstretch material maybe used. For example, fabric, non-woven fabric, polyurethane, polyester, polyvinyl acetate, polyvinylidene chloride, polyethylene, polyethylene terephthalate, aluminum sheet, etc., or composite materials thereof may be used.

In addition, as the release liner of the patch of the invention, in concrete terms, films such as polyesters (polyethylene terephthalate, etc.), polyvinyl chloride and polyvinylidene chloride, a laminated film of high-quality paper with polyolefin, and the like may be used. In these release liners, a fluorine treatment or a silicone treatment are preferably applied to the surface of the side attached to the adhesive layer of the release liner to facilitate operation in case of releasing the release liner from the adhesive side.

In the following, the invention is explained in more detail by examples. The invention, however, is not limited to these examples, and the sequence of blending of each ingredient is not particularly limited. In addition, various modifications may be possible without departing from the technical idea of the invention.

Test Example 1

Melting Point Measurement

About 1 g of risperidone and equivalent mole of the acid (acetic acid, lactic acid, benzoic acid or methanesulfonic acid) to each form ion-pair as the melting point lowering agent were measured, and added about 5 ml of dichloromethane as solvent to dissolve. The solution is left under room temperature to evaporate dichloromethane, and then after crystallization of each acid addition salt of risperidone, it is filtered to obtain crystals. Melting point measurement of the obtained crystals was carried out according to Japanese Pharmacopeia.

TABLE 1

| Risperidone | Melting Point (° C.) |
| --- | --- |
| Risperidone acetate | 42 |
| Risperidone lactate | 61 |
| Risperidone benzoate | 93 |
| Risperidone | 173 |
| Risperidone methanesulfonate | 194 |

As shown in Table 1, in the acetate (risperidone acetate), the lactate (risperidone lactate) and the benzoate (risperidone benzoate) of risperidone, the melting points fall remarkably compared with free base risperidone (risperidone). On the other hand, it is understood that in the addition salt of methanesulfonic acid (risperidone methanesulfonate), which is not the melting point lowering agent of the invention, the melting point rises compared with free base risperidone (risperidone).

EXAMPLE

The below ingredients in Table 2 were dissolved in toluene of solvent (the solid portion, 40 wt. %), then spread on a silicone-coated surface of a polyethylene terephthalate film (release liner, 75 μm), and dried at 70° C. for 10 min. Then, a backing polyethylene terephthalate film (sand-mat treatment, 25 μm) was laminated to obtain a risperidone-containing patch of the invention (the examples 1-13) and a risperidone-containing patch without containing a melting point lowering agent (the comparative examples 1-4). The thickness of the adhesive layers was each 70 μm.

Test Example 2

In Vitro Skin Permeability Test

A body part skin of a hairless mouse was removed, and then, the dermal side was placed to a receptor side and installed in a flow-through Franz type cell (3.14 cm$^2$) in which warm water of 32° C. was being circulated around the outer part. The patches of the invention (the examples 2,4 and 6-13) prepared as described above or the patches not containing the melting point lowering agents (the comparative examples 1-4) were attached to the horny layer side, and samplings were carried out every two hours for 24 hours at a rate of 5.5 ml/hr. As for the receptor layer, saline was used. The content of risperidone in a receptor solution at each hour was measured by a high-performance liquid chromatography method; the maximum permeation rate per hour of risperidone for each patch was calculated, showing the results in Table 3.

TABLE 2

| Example No. | SIS/ARKON P-100/Liquid paraffin (Composition weight ratio 10/35/10) % | Acrylic adhesive agent % | Risperidone % | Organic acid % | Mole ratio | Sodium acetate % | Mole ratio | IPM % | PGML % |
|---|---|---|---|---|---|---|---|---|---|
| Example 1 | 80.8 | a) 10.0 | 5.0 | Acetic acid 2.2 | 3.0 | 2.0 | 2.0 | — | — |
| Example 2 | 71.6 | a) 10.0 | 10.0 | Acetic acid 4.4 | 3.0 | 4.0 | 2.0 | — | — |
| Example 3 | 62.4 | a) 10.0 | 15.0 | Acetic acid 6.6 | 3.0 | 6.0 | 2.0 | — | — |
| Comparative Example 1 | 80.0 | a) 10.0 | 10.0 | — | — | — | — | — | — |
| Example 4 | 68.6 | a) 10.0 | 10.0 | Acetic acid 4.4 | 3.0 | 4.0 | 2.0 | 3.0 | — |
| Example 5 | 69.6 | a) 10.0 | 10.0 | Acetic acid 4.4 | 3.0 | 4.0 | 2.0 | — | — |
| Example 6 | 78.6 | — | 10.0 | Acetic acid 4.4 | 3.0 | 4.0 | 2.0 | 3.0 | — |
| Example 7 | 68.6 | a) 10.0 | 10.0 | Acetic acid 4.4 | 3.0 | 4.0 | 2.0 | — | 3.0 |
| Example 8 | 78.6 | — | 10.0 | Acetic acid 4.4 | 3.0 | 4.0 | 2.0 | — | 3.0 |
| Example 9 | — | b) 78.6 | 10.0 | Acetic acId 4.4 | 3.0 | 4.0 | 2.0 | — | 3.0 |
| Example 10 | — | a) 78.6 | 10.0 | Acetic acid 4.4 | 3.0 | 4.0 | 2.0 | — | 3.0 |
| Comparative Example 2 | — | a) 87.0 | 10.0 | — | — | — | — | — | 3.0 |
| Example 11 | 82.1 | — | 10.0 | Acetic acid 3.0 | 2.0 | 2.0 | 1.0 | — | 3.0 |
| Example 12 | 84.8 | — | 10.0 | Lactic acid 2.2 | 1.0 | — | — | — | 3.0 |
| Example 13 | 84.0 | — | 10.0 | Benzoic acid 3.0 | 1.0 | — | — | — | 3.0 |
| Comparative Example 3 | 87.0 | — | 10.0 | — | — | — | — | — | 3.0 |
| Comparative Example 4 | 84.7 | — | 10.0 | Methanesulfonic acid 2.3 | 1.0 | — | — | — | 3.0 |

All of the percentages (%) in Table 2 mean wt. %.

All of the mole ratios in Table 2 represent the mole ratio against risperidone.

a) Duro-Tak 87-4098 (National Starch) acrylate copolymer (having no polar functional group in the molecule)

b) Duro-Tak 87-2516 (National Starch) acrylate copolymer (having hydroxyl group in the molecule)

SIS: (Kleiton polymer) styrene-isoprene-styrene block copolymer

ARKON P-100: (Arakawa Chemical Industries) tackifying resin

IPM: Isopropyl myristate

PGML: Propylene glycol monolaurate

TABLE 3

| Example No. | Maximum skin permeation rate (μg/cm$^2$/hr) | Time for maximum permeation rate (hr) |
|---|---|---|
| Example 2 | 11.63 | >23 |
| Comparative example 1 | Not detectable | — |
| Example 4 | 40.84 | >23 |
| Example 6 | 12.65 | 21 |
| Example 7 | 40.96 | 20 |
| Example 8 | 61.51 | 15 |
| Example 9 | 6.66 | 19 |
| Example 10 | 4.72 | >23 |
| Comparative example 2 | 1.50 | >23 |
| Example 11 | 26.8 | 9 |
| Example 12 | 7.7 | 13 |
| Example 13 | 4.1 | 11 |
| Comparative example 3 | 2.4 | 13 |
| Comparative example 4 | 0.68 | 13 |

As shown in Table 3, in the patches of the comparative examples containing no melting point lowering agent, permeation to the skin was not detected (the comparative example 1) or it was scarcely detected (the comparative examples 2-4); on the contrary, in the patches of the invention (the examples 2,4 and 6-13) containing melting point lowering agents such as acetic acid, lactic acid orbenzoic acid, a very favorable skin permeability of risperidone was each observed. Thus, these results demonstrated that although a patch having a sufficient percutaneous absorbability and sustainability could not be obtained simply by making a drug, such as risperidone etc., contained in an adhesive layer which contained a known adhesive base or absorption enhancer, the percutaneous absorbability of the drug was significantly improved to give a patch sufficiently exerting a drug efficacy excellent in sustainability by preparing a patch in which the melting point lowering agent was contained in an adhesive layer together with the drug and making the drug exist in the adhesive layer in a form of the melting point lowering agent's addition salt.

In addition, considering the results in Table 3 with the results in Table 1, in the acetate of risperidone (risperidone acetate), the lactate of risperidone (risperidone lactate) and the benzoate of risperidone (risperidone benzoate), the melting points fall largely compared with the free base of risperidone (risperidone); the patches of the invention (the examples 1-13) containing risperidone as the addition salts of these melting point lowering agents are more than several times to several tens times higher in the skin permeation rate than the patches (the comparative examples 1-3) containing risperidone as free base, suggesting that melting-point lowering agent addition salts of risperidone had very excellent percutaneous absorbability compared with the free base. In the mean time, in the addition salt of methanesulfonic acid (risperidone methanesulfonate) which is not the melting point lowering agent of the invention, the melting point rises compared with free base risperidone (risperidone) the patch containing risperidone as methanesulfonate greatly decreases in the skin permeation rate, and therefore, it is understood that methanesulfonic acid does not improve the skin permeability of risperidone.

Further, in case of blending isopropyl myristate (IPM) or propylene glycol monolaurate (PGML) as an absorption enhancer (the examples 4 and 7), the skin permeability of the patches of the invention were furthermore improved (about 4 times) compared with the case (the example 2) where these were not contained.

In addition, in case using SIS, acrylate copolymer or both SIS and acrylate copolymer as the adhesive base, a favorable skin permeability of risperidone was obtained, respectively (the examples 1-13). Further, in case using acrylate copolymer, it was shown that the acrylate copolymer having a polar functional group (hydroxyl group) in the molecule (the example 9) was more excellent than the acrylate copolymer having no polar functional group in the molecule (the example 10). Furthermore, it became clear that the case using SIS only or the case using both SIS and acrylate copolymer showed more excellent percutaneous absorbability compared with the case using only acrylate copolymer.

The above results showed that the percutaneous absorbability of a specific drug was significantly improved by a melting point lowering agent used in the invention, and it also became clear that a patch of the invention, in which the melting point lowering agent was contained with the specific drug in an adhesive layer, was excellent in the skin permeability, had no problem in the stability of the pharmaceutically effective ingredient in the preparation and could exert a sustained drug efficacy. In addition, it became clear that a patch having a more excellent skin permeability could be provided by blending an absorption enhancer such as isopropyl myristate (IPM), propylene glycol monolaurate (PGML), lauric diethanolamide or capric acid, in the patch containing the drug and its melting point lowering agent. Further, it was demonstrated that using SIS and/or acrylate copolymer as an adhesive agent in such a patch resulted in providing a patch having extremely excellent skin permeability and sustainability of the drug efficacy.

INDUSTRIAL APPLICABILITY

As explained above, according to the invention, a patch with extremely excellent skin absorbability of a drug in a preparation and excellent sustainability of the drug efficacy can be provided, and therefore, the patch of the invention is expected as a pharmaceutical preparation which can achieve easiness of the administration method and improvement of compliance as well as can be used for therapy of patients.

The invention claimed is:

1. A patch containing a drug selected from the group consisting of oxybutynin, fentanyl, pergolide, tandospirone, donepezil, tamsulosin, risperidone, flurazepam, butorphanol, perisoxal, pridinol, trihexyphenidyl, amantadine, tulobuterol, isoprenaline, propranolol, ketotifen, difenidol, morphine, meloxicam, valdecoxib and celecoxib, an adhesive base, at least one melting point lowering agent that lowers the melting point of the drug to increase skin permeation rate of the drug, wherein the melting point lowering agent is one or more selected from the group consisting of acetic acid, propionic acid, butyric acid, lactic acid, benzoic acid and salicylic acid, and a corresponding salt of the melting point lowering agent.

2. The patch according to claim 1, wherein the melting point lowering agent lowers the melting point of the drug by 60° C. or more.

3. The patch according to claim 1, wherein the melting point lowering agent is acetic acid and the corresponding salt is sodium acetate.

4. The patch according to claim 1, wherein the adhesive base contains a styrene-isoprene-styrene block copolymer and/or an acrylate copolymer.

5. The patch according to claim 1, wherein said patch contains one or more absorption enhancers selected from a group consisting of lauric acid diethanolamide, capric acid, isopropyl myristate and propylene glycol monolaurate.

6. The patch according to claim 1 wherein the melting point lowering agent is in an amount of 0.5-5 mole against 1 mole of drug.

7. The patch according to claim 1 wherein the amount of the melting point lowering agent is 1-3 moles against 1 mole of the drug.

8. The patch according to claim 1, wherein the salt of the melting point lowering agent is in an amount of 0.5-5 mole against 1 mole of the drug.

9. The patch according to claim 8, wherein the amount of the salt of the melting point lowering agent is 2-3 mole against 1 mole of drug.

* * * * *